(12) United States Patent
Morine

(10) Patent No.: US 6,684,882 B1
(45) Date of Patent: Feb. 3, 2004

(54) RESPIRATOR

(76) Inventor: Kenneth R. Morine, 11 Davis Rd., Tyngsboro, MA (US) 01879

( * ) Notice: Subject to any disclaimer, the term of this patent is extended or adjusted under 35 U.S.C. 154(b) by 0 days.

(21) Appl. No.: 10/098,599

(22) Filed: Mar. 15, 2002

(51) Int. Cl.[7] .................. A61G 10/00; A61M 16/00; A62B 7/10; A62B 23/02
(52) U.S. Cl. ...................... 128/206.11; 128/203.22; 128/206.18; 128/207.18
(58) Field of Search ............. 128/205.12, 205.29, 128/206.12, 206.18, 207.18, 203.22, 204.12, 205.27, 206.11, 207.13

(56) References Cited

U.S. PATENT DOCUMENTS

| | | | |
|---|---|---|---|
| 718,785 A | | 1/1903 | McNary |
| 781,516 A | * | 1/1905 | Gutherie ................ 128/206.18 |
| 1,443,820 A | | 1/1923 | Hudson |
| 2,693,800 A | * | 11/1954 | Caldwell ............... 128/207.18 |
| 3,513,844 A | * | 5/1970 | Smith .................... 128/207.18 |
| 3,884,223 A | * | 5/1975 | Keindl ................... 128/206.11 |
| 3,902,486 A | * | 9/1975 | Guichard .............. 128/203.22 |
| 4,106,505 A | | 8/1978 | Salter et al. |
| 4,422,456 A | | 12/1983 | Tiep |
| 4,665,566 A | | 5/1987 | Garrow |
| 4,782,832 A | * | 11/1988 | Trimble et al. ........ 128/207.18 |
| 4,915,105 A | * | 4/1990 | Lee ........................ 128/205.27 |
| 4,938,211 A | * | 7/1990 | Takahashi et al. ..... 128/204.26 |
| 4,996,983 A | | 3/1991 | AmRhein |
| 5,113,857 A | | 5/1992 | Dickerman et al. |
| 5,425,359 A | | 6/1995 | Liou |
| 5,603,317 A | * | 2/1997 | Farmer .................. 128/205.27 |
| 5,720,280 A | * | 2/1998 | Elstran et al. ......... 128/205.25 |
| 5,769,702 A | * | 6/1998 | Hanson ....................... 454/63 |
| 6,012,455 A | * | 1/2000 | Goldstein .............. 128/207.18 |
| 6,216,694 B1 | | 4/2001 | Chen |
| 6,478,026 B1 | * | 11/2002 | Wood .................... 128/207.18 |

* cited by examiner

*Primary Examiner*—Weilun Lo
*Assistant Examiner*—Michael Mendoza
(74) *Attorney, Agent, or Firm*—O'Connell Law Firm

(57) ABSTRACT

A respirator for enabling a wearer to inhale filtered air through the wearer's nostrils comprising an elongate breathing tube, an air-purifying element disposed in fluidic engagement with the elongate breathing tube, and first and second nasal inserts disposed in fluidic engagement with the elongate breathing tube and with the air-purifying element. The first and second nasal inserts are preferably disposed in close proximity to one another, and a nose plug preferably extends from each nasal insert. With this, a wearer can inhale purified air into the wearer's nostrils through the nose plugs from the elongate breathing tube after the air has been purified by being drawn through the air-purifying element.

42 Claims, 4 Drawing Sheets

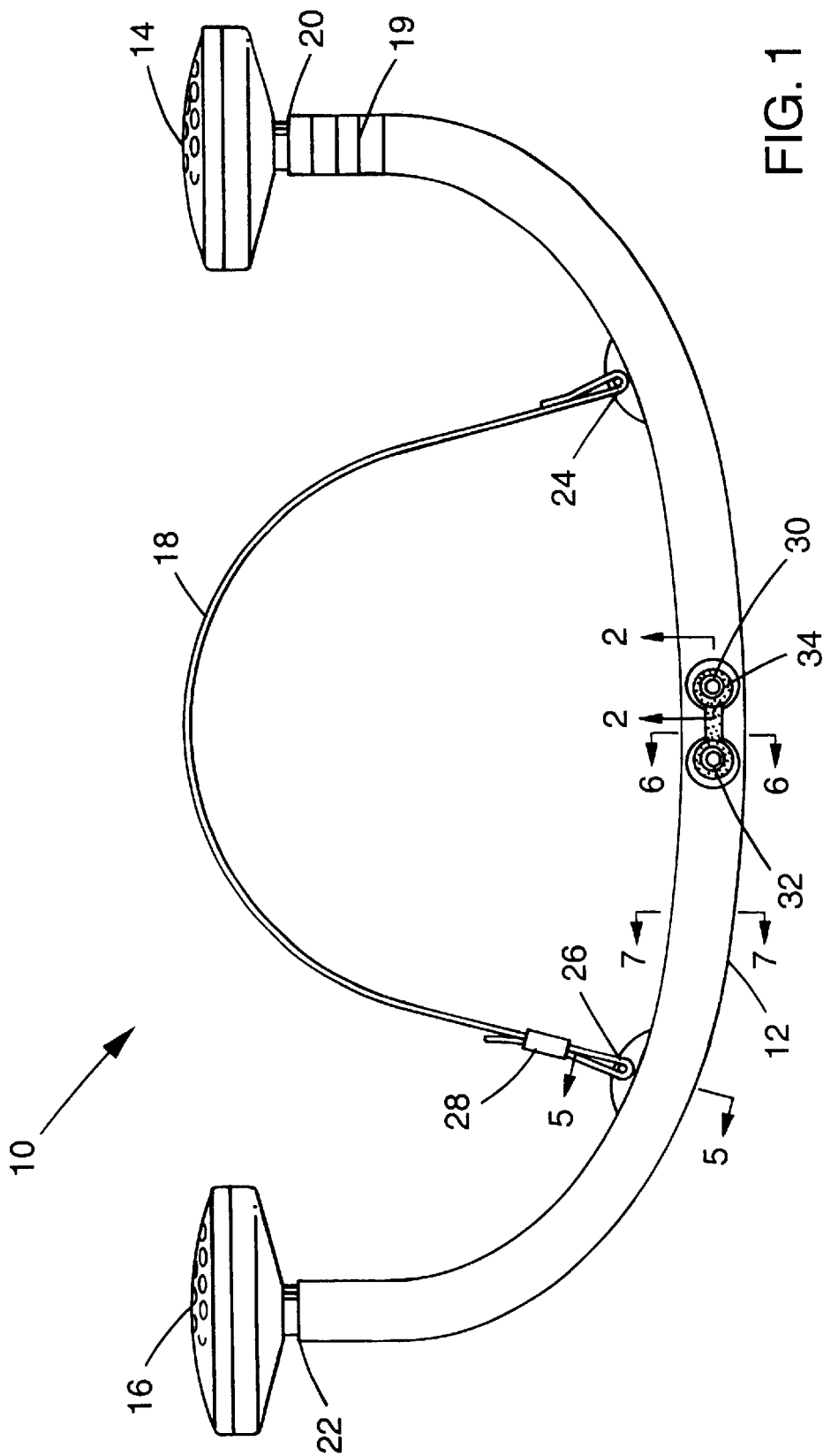

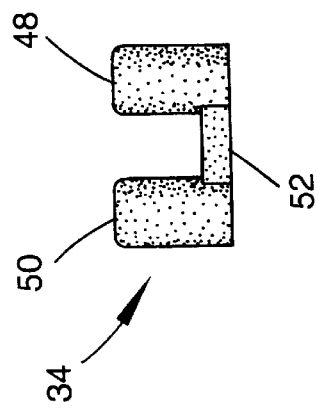
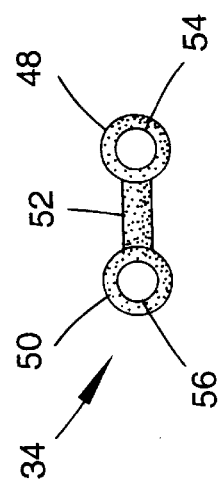
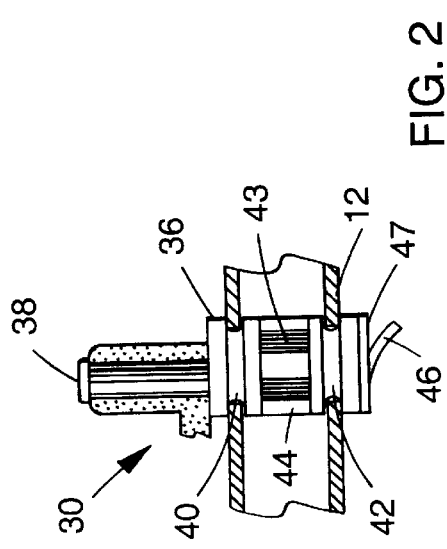
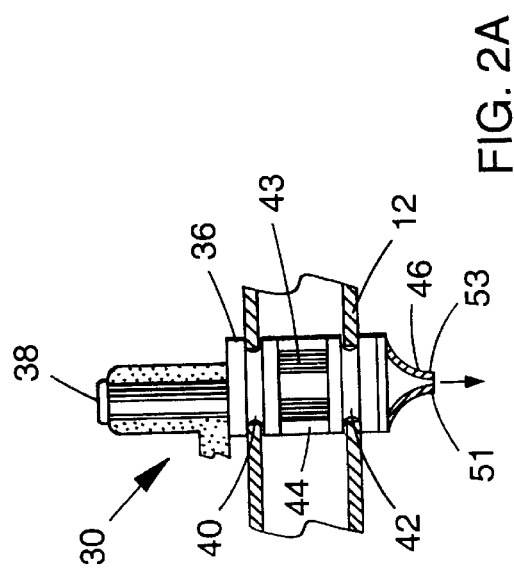

RESPIRATOR

FIELD OF THE INVENTION

The present invention relates generally to devices for enabling filtered respiration. Stated more particularly, this patent discloses and protects a respiratory device that enables filtered air to be breathed directly through the nostrils of a wearer.

BACKGROUND OF THE INVENTION

Respirators are desirable, indeed necessary, in a wide variety of circumstances for purifying or otherwise improving air contaminated with harmful dusts, fogs, fumes, mists, gases, smokes, sprays, or vapors. For example, the materials and tools used by plumbers, welders, and other workers commonly produce noxious and potentially dangerous fumes that, at the very least, make the wearing of a respirator for providing purified air desirable. Indeed, with regard to the United States, the Occupational Safety & Health Administration (OSHA) has promulgated regulations, which are set forth in 29 C.F.R. 1910.134, demanding that appropriate respirators be used in the control of occupational diseases caused by atmospheric contamination.

As one would expect, therefore, the prior art has disclosed a multitude of filters for providing a wearer with a safely breathable air supply. The filters remove specific contaminants from ambient air by passing that air through an air-purifying element. To date, the great majority of prior art filters have enveloped the nose, mouth, and, possibly, eyes of the wearer. For example, one common filter is a filtering facepiece, commonly referred to as a dust mask, which is a negative pressure particulate respirator wherein a filter is an integral part of the facepiece or wherein the entire facepiece is composed of the filtering medium. A second type of filter is termed an air-purifying respirator, which has a framework that removably and replacably retains a canister or cartridge. The canister or cartridge, in turn, comprises a container with a filter, sorbent, or catalyst, or combination thereof that removes specific contaminants from the air passed through the container. Each type of filter certainly has demonstrated ample utility in improving the safety of the wearer.

Unfortunately, the filters and respirators of the prior art suffer from a number of disadvantages. Dust masks, for example, are primarily useful for filtering bulk particulate matter from air and are generally not useful relative to air contaminated with fumes. As a result, they are of little use to purify air of the fumes produced, by way of example, by certain plumbing materials and during certain welding operations. Air purifying respirators, for their part, tend to be bulky, heavy, and awkward and often interfere with the wearer's field of vision. Even further, both dust masks and air-purifying respirators entirely cover the wearer's nose and mouth. With this, they can become hot and uncomfortable during use. Furthermore, they effectively prevent the wearer from speaking, eating, drinking, and otherwise performing tasks requiring the use of his or her mouth.

As a result, many workers participating in endeavors involving air contaminated with hazardous materials nonetheless refuse or neglect to wear a filter or respirator notwithstanding the resulting dangers to their lungs, throat, and health in general. With this, workers exposed to air contaminated with particles, such as from grinding machines, sanding equipment, or asbestos, and workers exposed to chemical pollutants, such as welding, painting, and plumbing fumes, for example, forego wearing the cumbersome filters or respirators. Consequently, the effectiveness and utility of the prior art devices become entirely obviated as they sit in the worker's toolbox.

With these things in mind, it becomes clear that there is a substantial need in the art for a filtration device that is effective in filtering particles, fumes, and other contaminants from ambient air while being comfortable and unobtrusive during use.

SUMMARY OF THE INVENTION

Advantageously, the present invention has as its primary object the provision of a respirator that meets each of the needs that the prior art has left unmet while providing a number of further advantages thereover.

More particularly, a most basic object of the present invention is to provide a respirator that is effective in purifying air of contaminants thereby to provide a wearer with a safely breathable air supply.

Another fundamental object of the invention is to provide a respirator that is comfortable and non-obstructive during use.

A related, and possibly most critical, object of the invention is to provide a respirator that prospective wearers will be encouraged to use and wear such that its true utility can be realized.

These and further objects and advantages will become obvious not only to one who reviews the present specification and drawings but also to one who has an opportunity to make use of an embodiment of the present invention for a respirator.

In carrying forth the foregoing objects, a basic embodiment of the present invention comprises a respirator with an elongate breathing tube, an air-purifying element disposed in fluidic engagement with the elongate breathing tube for purifying air that is drawn through the first air-purifying element, and first and second nasal inserts disposed in fluidic engagement with the elongate breathing tube and with the first air-purifying element. The first and second nasal inserts preferably will be disposed in close proximity to one another, and a nose plug ideally will extend from each of the first and second nasal inserts. Under this arrangement, a wearer can insert the nose plugs into his or her nostrils so that he or she can inhale purified air into his or her nostrils through the nose plugs from the elongate breathing tube after the air has been purified by being drawn through the air-purifying element.

In certain embodiments, the air-purifying element can be coupled to a distal end of the elongate breathing tube. Also, the elongate breathing tube can have two distal ends with an air-purifying element coupled to each distal end and the first and second nasal inserts disposed in a proximal portion of the breathing tube. Even more preferably, embodiments of the invention can incorporate a means for rendering the body portion of the elongate tube capable of exhibiting plastically deformable shape retention. With that, the relative shape and orientation of the elongate tube and the location and orientation of the air-purifying element or elements can be selectively adjusted.

The means for rendering the body portion of the elongate tube capable of exhibiting plastically deformable shape retention could take a number of forms, each well within the scope of the present invention. For example, the shape retention means could comprise an elongate core member, such as a strand of metal wire. The core member can be longitudinally associated with the elongate tube, such as by being embedded therein. Alternatively, the means for rendering the body portion of the elongate tube capable of exhibiting plastically deformable shape retention could be realized by a material selection for at least part of the body portion of the elongate tube. To enable and guide any necessary or desirable trimming of the length of the elongate tube, guide or score lines could be spaced along the body portion of the breathing tube.

In preferred embodiments of the respirator, the first and second nasal inserts can be rotatably retained relative to the elongate tube, and the nose plugs can be eccentrically disposed relative to the first and second nasal inserts. Under this arrangement, the effective distance between the first and second nose plugs can be selectively adjusted by a rotation of one or both of the first and second nasal inserts. With this, the respirator can accommodate the ergonomic concerns and preferences of wearer's with differing characteristics and preferences.

The first and second nasal inserts could also have valved exhaust apertures associated therewith so that air can be exhaled from the wearer's nostrils and through the exhaust valve in a low-pressure arrangement. The exhaust valve could preferably comprise a one-way valve to prevent unfiltered air from entering the breathing tube.

In certain embodiments, the respirator could further include a means for preventing unfiltered air from passing between the nose plugs and the wearer's nostrils. Of course, that means could take a plurality of forms within the scope of the present invention. For example, the means could comprise first and second sealing sleeves, possibly coupled by a bridge member, for surrounding the nose plugs and thereby being interposed between the wearer's nostrils and the nose plugs. The first and second sealing sleeves can be formed from a resiliently compressible material, such as viscoelastic foam.

The air-purifying element or elements also could take many forms under the present invention. In one embodiment, the air-purifying element or elements each comprise a canister casing that retains a volume of filtering material. In such a case, the air-purifying element or elements can each have a male projection extending therefrom for matingly engaging a distal end of the breathing tube. Even further, positive engaging elements, such as ridges or threads, can be disposed on the male projection for better retaining the air-purifying element relative to the breathing tube.

Preferred embodiments of the respirator will even further include a retaining strap for securing the breathing tube to a wearer's head. First and second ends of the retaining strap could be retained by a post that could be removably and replacably coupled to the breathing tube. Also, the first and second ends of the retaining strap can be removably and replacably associated with the post. With this, the first and second ends of the retaining strap can be removed and replaced relative to the breathing tube to allow for any necessary repair, replacement, or other manipulation.

In certain cases, such as where desired by the wearer or required by regulation, the respirator could additionally include a mouthpiece coupled to the breathing tube for shielding a wearer's mouth. Where provided, the mouthpiece could comprise a filtering mouthpiece, which would be similar in structure and operation to a traditional dust mask, or it could comprise a non-porous, sealed mouthpiece. In any case, the respirator could comprise a negative pressure respirator or any other type of respirator that could incorporate aspects of the present invention.

One will appreciate that the foregoing discussion broadly outlines the more important features of the invention to enable a better understanding of the detailed description that follows and to instill a better appreciation of the inventor's contribution to the art. Before an embodiment of the invention is explained in detail, it must be made clear that the following details of construction, descriptions of geometry, and illustrations of inventive concepts are mere examples of the many possible manifestations of the invention.

BRIEF DESCRIPTION OF THE DRAWINGS

In the accompanying drawing figures:

FIG. 1 is a top plan view of a respirator according to the present invention;

FIG. 2 is a cross-sectional view of a nasal insert of the respirator of FIG. 1 taken along the line 2—2;

FIG. 2A is a cross-sectional view of an alternative nasal insert of the respirator of FIG. 1 again taken along the line 2—2;

FIG. 3 is a view in side elevation of a nasal insert cover according to the present invention;

FIG. 4 is a top plan view of the nasal insert cover of FIG. 3;

DETAILED DESCRIPTION

Figure 5:
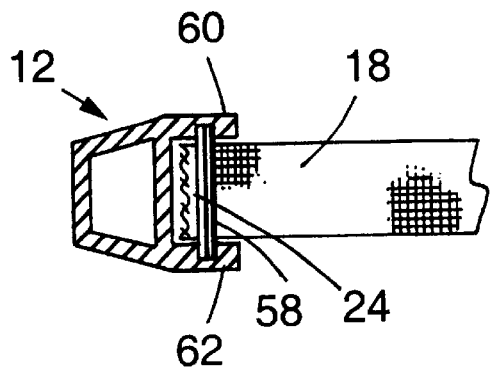
FIG. 5 is a cross-sectional view of a retaining strap connection with a breathing tube according to the present invention.

As is the case with many inventions, the present invention for a respirator is subject to a wide variety of embodiments. However, to ensure that one skilled in the art will be able to understand and, in appropriate cases, practice the present invention, certain preferred embodiments of the broader invention revealed herein are described below and shown in the accompanying drawing figures.

Looking more particularly to the drawings, a preferred embodiment of the present invention for a respirator is indicated generally at 10 in FIG. 1. There, one sees that the respirator 10 is founded on an elongate breathing tube 12 that terminates in a first end 20 and a second end 22. A first air-purifying element 14 is sealingly engaged with the first end 20 of the breathing tube 12, and a second air-purifying element 16 is sealingly engaged with the second end 22 of the breathing tube 12. An elongate, flexible retaining strap 18 for securing the breathing tube 12 to a wearer's head has a first end 24 coupled to a mid-portion of what may be considered a first branch of the breathing tube 12 that terminates at the first end 20 of the breathing tube 12 and a second end 26 coupled to a mid-portion of a second branch of the breathing tube 12 that terminates at the second end 22 of the breathing tube 12. A first nasal insert 30 and a second nasal insert 32 are disposed in close proximity to one another to opposite sides of a mid-point of the breathing tube 12 in general. Finally, a nasal insert cover 34 is received over the first and second nasal inserts 30 and 32.

Figure 6:
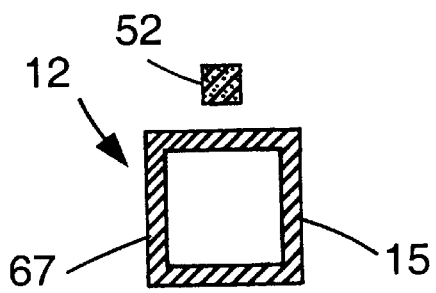
FIG. 6 is a cross-sectional view of the breathing tube of FIG. 1 taken along the line 6—6.
Figure 7:
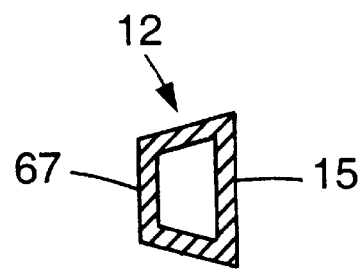
FIG. 7 is a cross-sectional view of the breathing tube of FIG. 1 taken along the line 7—7.
Figure 7A:
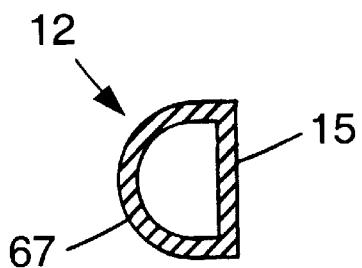
FIG. 7A is a cross-sectional view of a breathing tube with a alternative cross section.
Figure 8:
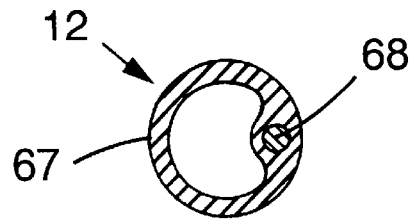
FIG. 8 is a cross-sectional view of an alternative breathing tube according to the present invention.
Figure 9:
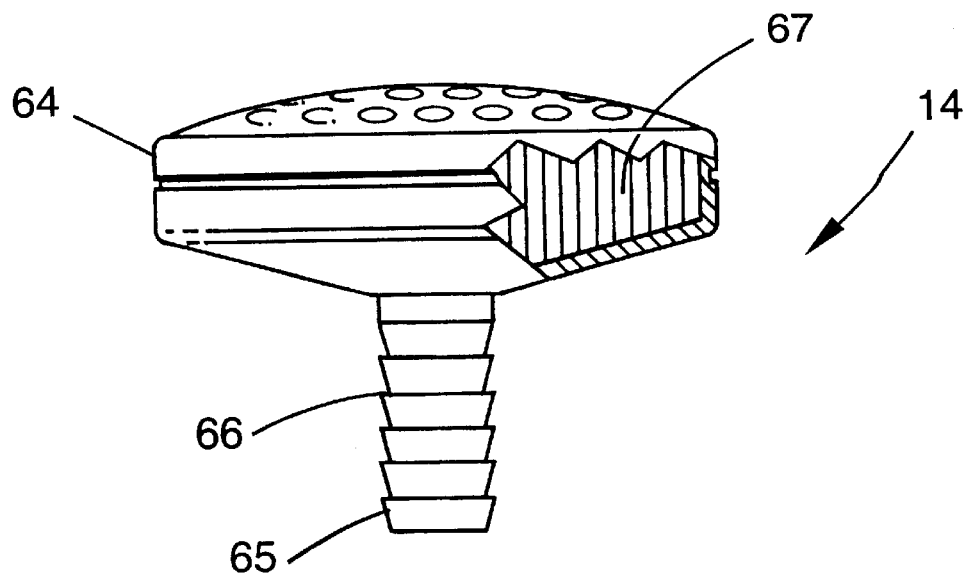
FIG. 9 is a view in side elevation of a filtration canister according to the present invention.

In this exemplary embodiment of the respirator 10, the breathing tube 12 is crafted as a single member forming the first and second branches. Of course, the breathing tube 12 could have a variety of cross-sectional shapes within the scope of the present invention. For example, the breathing tube 12 could be oval or round in cross section as shown in FIG. 8, it could be rectangular in cross section with a flat proximal surface 15 as shown in FIG. 6, it could simply have a quadrilateral cross section again with a flat proximal surface 15 as shown in FIG. 7, it could have a flat side 15 and an arched portion as shown in FIG. 7A, or it could have substantially any other cross sectional shape. In any event, it will be noted that, in embodiments where a flat proximal wall 15 is provided, the breathing tube 12 or section of the breathing tube 12 advantageously will present a comfortably flat surface for contacting the wearer's face.

Figure 10:
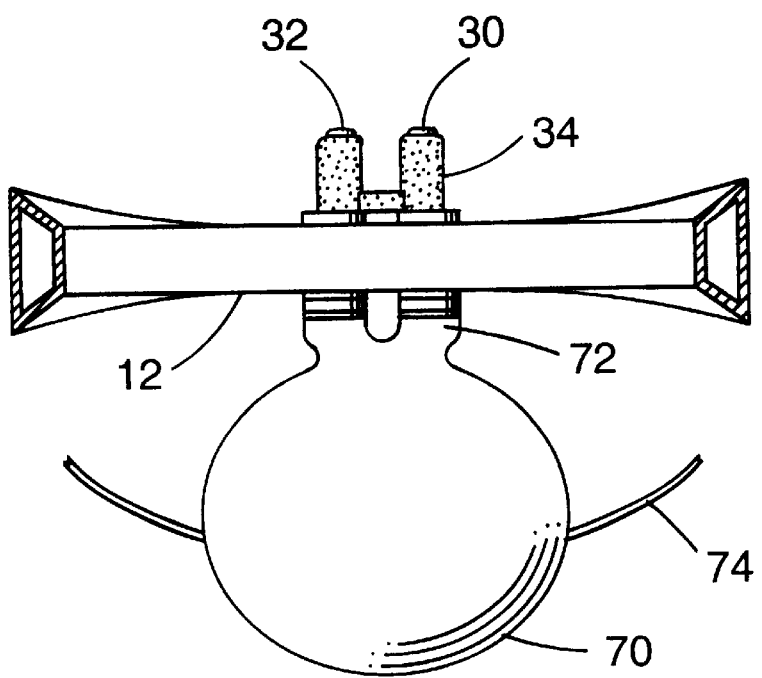
FIG. 10 is a view in front elevation of a portion of alternative respirator according to the present invention.

Furthermore, although it will be clear that the breathing tube 12 could have a uniform cross section along its entire length, it may be preferable in certain embodiments of the invention to vary the cross section of the breathing tube 12 to accommodate, among other things, ergonomic concerns relative to a wearer's face. For example, assuming the width of the breathing tube 12 to be measured from what would be the upper surface of the breathing tube 12 in the top plan view of FIG. 1 to the opposite lower surface, the breathing tube 12 could be crafted to have a relatively narrowed portion in the area of the first and second nasal inserts 32 and 34, and the breathing tube 12 can progressively widen as the distance from the first and second nasal inserts 32 and 34 increases. One embodiment of such a construction is depicted in FIG. 10. By being narrower where the breathing tube 12 will typically rest below a wearer's nose, the breathing tube 12 advantageously will tend to fit more comfortably between the wearer's nose and mouth.

In particularly unique embodiments, the first and second branches of the breathing tube 12 can incorporate a means for rendering the first and second branches capable of exhibiting plastically deformable shape retention. Stated alternatively, the preferred first and second branches will be plastically deformable but capable of substantially maintaining a given configuration once adjusted to that configuration by a user. With this, a user can adjust the relative shape and orientation of the first and second branches and the location and orientation of the first and second air-purifying elements 14 and 16. Accordingly, the user will be able to manipulate the first and second branches and the first and second air-purifying elements 14 and 16 to accommodate his or her ergonomic and environmental concerns, and the first and second branches can be readjusted as necessary or desired. Of course, the amount of force necessary to reconfigure the first and second branches can be calibrated during design and manufacture.

This plastically deformable shape retention of the first and second branches and the breathing tube 12 in general could be achieved in a plurality of ways that each are well within the scope of the present invention whether or not expressly disclosed herein. For example, as is shown in the cross-sectional view of FIG. 8, the first and second branches can be formed with a core member 68 embedded in or otherwise longitudinally associated with a flexible tube member 67. The core member 68 preferably will be formed from a length of tough, bendable material capable of generally maintaining itself and the flexible tube member 67 in a given configuration once so manipulated.

Of course, one knowledgeable in the art will be aware of a number of materials that could well be used to form the core member 68. Just as clearly, one must appreciate that suitable materials may well be developed after the writing of the present disclosure. All such materials should be considered to be within the scope of this disclosure's use of the phrase plastically deformable shape retaining material and within the scope of the present invention. Presently known materials that would be suitable include, among others, properly selected metals and metal alloys, such as copper in wire form; polymeric materials, such as plastic; and a variety of other materials.

It should also be clear that, although the core member 68 is shown as being generally round in cross section in FIG. 8, the core member 68 could well have any one of a virtually infinite variety of other configurations including being ribbon shaped or oval. Even further, it is possible that the core member 68 could be formed in multiple sections, which could be disjointed or possibly hingedly connected. Furthermore, although just one core member 68 is shown in FIG. 8, additional core members 68 could be included whether they be side by side with one another or spaced around the tube member 67.

Similarly, the tube member 67 could be formed from any suitable material and could be crafted with numerous different cross sectional shapes. With this, one will appreciate that, although the term tube is used herein, the tube member 67 need not necessarily be round, oval, or any particular shape unless otherwise specified. Possible materials for the tube member 67 include polymeric materials, such as rubber or a plastic, such as polyvinyl chloride. The tube member 67 could be extruded, molded, or formed by any other suitable method. Where possible, such as when polyvinyl chloride is employed, the durometer, durability, and flexibility of the material can be manipulated by appropriate material composition, such as by the addition of plasticizers.

Indeed, as FIGS. 6, 7, and 7A show, embodiments of the respirator 10 can be crafted where the desired plastically deformable shape retention is achieved by the material composition of the tube member 67. With this, the first and second branches of the breathing tube 12 could be crafted with no core member 68. For example, a polymer, such as polyvinyl chloride, or other composition could be crafted that would be capable of retaining user-manipulated shapes. Of course, one knowledgeable in the art would be aware of other material compositions that could achieve the preferred plastically deformable shape retention.

Turning to FIG. 2, one sees a sectioned view of a portion of the breathing tube 12 exposing the first nasal insert 30, which is in substance identical to the second nasal insert 32. In this exemplary embodiment, the nasal insert 30 has a body portion 36 that passes entirely through corresponding apertures in the breathing tube 12 such that it passes from what for present purposes will be considered the upper edge to the lower edge of the breathing tube 12. The body portion 36 of the nasal insert 30 is generally tubular and has an upper annular furrow 40 adjacent to its upper end and a lower annular furrow 42 adjacent to its lower end. The upper and lower furrows 40 and 42 preferably tightly receive or are otherwise engaged with the inner annular edges of the apertures in the breathing tube 12 in a tight, sealing relationship.

Between the upper and lower furrows 40 and 42, and therefore within the breathing tube 12, the body portion 36 of the nasal insert 30 has at least one opening 43, which may or may not have a valve (not shown) associated therewith, for allowing air to be drawn into and expelled from the inner volume of the body portion 36. Of course, the opening 43 could take nearly an infinite number of forms. In this embodiment, there are plural openings 43 formed between a plurality of spaced columns 44 that form the central portion of the body portion 36 of the nasal insert 30.

As FIG. 2 shows with regard to the first nasal insert 30, the lower end of the body portion 36 of each of the first and second nasal inserts 30 and 32 has a low-pressure exhaust aperture 47 disposed external to the breathing tube 12. To prevent unfiltered air from entering the nasal insert 30 and the respirator 10 in general, a one-way valve 46 is operably associated with the exhaust aperture 47. It will be appreciated that the one-way valve 46 could be of any operable construction. In the exemplary embodiment of FIG. 2, the one-way valve 46 is a simple flapper valve, also indicated at 46, wherein a thin, flexible member, such as a disc of rubber, has a fixed portion fastened to the nasal insert 30 and a free portion for flapping outwardly as shown in FIG. 2 to allow the exhaustion of air. However, the flapper valve 46 is normally closed and is still more securely closed when a negative pressure is induced within the breathing tube 12. With this, unfiltered air is entirely prevented from entering the breathing tube 12 while exhaled air can readily pass out of the breathing tube 12 through the one-way valve 46.

Again, the type of one-way valve 46 can be varied well within the scope of the present invention, and a variety of valve types and constructions, whether now existing or hereafter developed, will readily occur to one skilled in the art after reviewing the present disclosure. For example, the one-way valve 46 could readily be a diaphram-type valve, a floating ball-type one-way valve, and any other suitable valve. An even better understanding of the many types of valves that could be used under the present invention can be had by reference to, for example, U.S. Pat. Nos. 2,865,369, 853,431, and 769,755, which are incorporated herein by reference.

An alternative one-way valve 46 is depicted in FIG. 2A. There, the one-way valve 46 simply comprises a first and second opposed lips 51 and 53 that are formed of resiliently flexible material, such as rubber. The lips 51 and 53 are in a normally-contacting relationship but can spread apart when a fluid is driven in the direction of the arrow in FIG. 2A. The lips 51 and 53 advantageously allow air to be expelled from the nasal insert 30 and the respirator 10 in general in the direction of the arrow by spreading apart. However, when a user seeks to draw air through the nasal inserts 30 and 32, the lips 51 and 53 are pressed still tighter together thereby preventing air from entering the respirator 10. With this, a remarkably simple yet effective one-way valve 46 is provided.

Again looking to FIG. 2, where the first nasal insert 30 is shown as exemplifying each of the first and second nasal inserts 30 and 32, one will see that a nose plug 38 extends from the upper end of each of the nasal inserts 30 and 32. In use, each nose plug 38 is inserted directly into a wearer's nostril. Advantageously, each nose plugs 38 is eccentrically located relative to its respective nasal insert 30 or 32. With this, since the nasal inserts 30 and 32 are rotatably retained in the annular apertures in the breathing tube 12, the distance between the nose plugs 38 can be readily adjusted by a rotation of one or both of the first and second nasal inserts 30 and 32. Under this arrangement, therefore, the respirator 10 can be adapted to accommodate wearer's of a wide variety of ergonomic characteristics and preferences.

For most effective function, each nose plug 38 should engage its respective nostril in a sealing relationship such that unfiltered air cannot pass around the nose plug 38 to enter the wearer's nostril. This too could be accomplished by a plurality of means. In this embodiment, the means for preventing unfiltered air from passing between the nose plugs 38 and the wearer's nostrils is provided in the form of first and second sealing sleeves 48 and 50 that surround the nose plugs 38 of each of the first and second nasal inserts 30 and 32 as one can see most clearly in FIGS. 1 and 10.

Although they certainly need not be to be within the scope of the present invention, the first and second sealing sleeves 48 and 50 are connected by a bridge 52 to form the nasal insert cover 34. The first and second sealing sleeves 48 and 50 preferably are capable of being selectively removed from the nose plugs 38, such as by sliding. Advantageously, with the bridge 52 connecting them, the first and second nasal inserts 30 and 32 are unlikely to become lost individually and are prevented from being inadvertently drawn into a user's nose. The first and second sealing sleeves 48 and 50 and the connecting bridge 52 could be formed individually and joined by any appropriate means to form the nasal insert cover 34. Alternatively, the first and second sealing sleeves 48 and 50 and the connecting bridge 52 could be created initially as a single unit as the nasal insert cover 34.

Preferably, the first and second sleeves 48 and 50 and, possibly, the connecting bridge 52 will be formed from a resiliently compressible material, such as foam. Even more particularly, the material for the first and second sleeves 48 and 50 will be a viscoelastic material. By way of example and not limitation, the first and second sleeves 48 and 50 and the connecting bridge 52 could be formed from a resiliently compressible foam material, such as a foam polymer of rubber, polyurethane, plasticized polyvinylchloride, or, possibly even more preferably, polyether polyurethane foam for its generally soft surface feel. The polyether polyurethane foam compositions could be based on polyurethane prepolymers blended with acrylic latex modifiers. For example, such polyether polyurethane prepolymers are currently available from the W. R. Grace Company under the "HYPOL" brand name while suitable acrylic latex modifiers are available from the Union Carbide Corporation under the "UCAR" brand name.

Under such an arrangement, a user would compress the first and second sleeves 48 and 50, such as by pinching them, rolling them, or compressing them by any other appropriate method. This could be done either with the first and second sleeves 48 and 50 disposed over the first and second nasal inserts 30 and 32 or with the first and second sleeves 48 and 50 removed therefrom and then applied to the first and second nasal inserts 30 and 32 while still compressed. With this, the first and second sleeves 48 and 50 would function relative to the wearer's nose much like earplugs function relative to a wearer's ears. More particularly, with the first and second sleeves 48 and 50 compressed and disposed on them, the first and second nasal inserts 30 can be inserted into the wearer's nostrils whereupon the first and second sleeves 48 and 50 will tend to expand slowly to their original volume thereby entirely occupying the wearer's nasal passages.

In this exemplary embodiment, each of the first and second air-purifying elements 14 and 16 comprise a canister casing 64 that retains a volume of filtering material 67. The air-purifying elements 14 and 16 also have a male projection 65 extending therefrom for matingly engaging the first and second ends 20 and 22 of the breathing tube 12. The male projection 65 preferably has ridges or threads or other positive engaging elements 66 disposed thereon for positively engaging the first and second ends 20 and 22 of the breathing tube 12. Most advantageously, under this arrangement, a user can readily remove and replace the first and second air-purifying elements 14 and 16 relative to the first and second ends 20 and 22 of the breathing tube 12.

Furthermore, if necessary or desirable, the user can trim the length of the first and second branches of the breathing tube 12, such as by cutting with a knife, scissors, or any other appropriate means. With this, the user can adjust the overall location of the first and second air-purifying elements 14 and 16. To enable and guide the user's cutting of the first and second branches of the breathing tube 12, the first and second branches could have score or guide lines 19 spaced therealong.

One will appreciate that the first and second air-purifying elements 14 and 16 could be of a wide variety of constructions depending, for example, on a plurality of workplace and user factors including the nature of the respiratory hazard(s) expected to be encountered and the chemical state and physical form of the contaminants to be filtered. Most basically, the first and second air-purifying elements 14 and 16 should comprise a means for removing contaminants, such as airborne particulates, droplets, or vapors, from the filtered air. As such, they could comprise, by way of example, any appropriate filter, cartridge, or canister that removes contaminants by passing ambient air through the air-purifying elements 14 and 16.

Where necessary, for example, the air-purifying elements 14 and 16 could comprise high efficiency particulate air (HEPA) filters in that they would be at least 99.97% efficient in removing monodisperse particles of 0.3 micrometers in diameter. The volume of filtering material 67 could be multi-layered or single layered. Where the filtering material is multi-layered the number, type, size and composition of the constituent layers again could vary. For example, the filtering material 67 could comprise commercially available fiberglass or HEPA pads and chemical cartridges. If chemical cartridges are to be employed, they ideally will be of the type approved by the National Institute of Occupational Safety and Health (NIOSH) for either a single type of toxic agent (for example, pesticide, organic vapor, acid gas or formaldehyde) or for multiple types of toxic agents (for example, organic vapors and acid gases, ammonia and methylamine, or acid gases and formaldehyde), depending on the needs of the user.

Additionally or alternatively, the filtering material 67 could comprise particulate-type filtering media such as activated carbon, molecular sieve material, or silica gel that could he held in place by appropriate packaging, screening, or the like. The filtering material 67 could contain adsorbents as in activated carbon, such as coal-, peat- or coconut-based activated carbon, for the physical adsorption of toxic agents such as organic vapors and or various types of impregnated carbons, such as sodium hydroxide, potassium iodide and zinc chloride impregnated carbon, for the chemisorption of toxic agents such as acid gases, formaldehyde, ammonia and methylamine. Of course, to broaden the range of toxic agents against which the filtering material 67 would be effective "dual fill" cartridges could be employed with a layer of an activated carbon and a layer of impregnated activated carbon. In any event, it will be clear that, by choosing appropriate volumes and combinations of filtering media, the first and second air-purifying elements 14 and 16 can be used to filter a wide range of airborne chemical and particulate contaminants.

The elongate, flexible retaining strap 18, which is preferably included for securing the breathing tube 12 to a wearer's head, also could be of a wide variety of constructions. Most basically, it can be any type of band, strip, or other elongate member that can effectively retain and support the breathing tube 12. Preferably, as one can perceive from FIGS. 1 and 5, the retaining strap 18 will be of a relatively wide construction and will be crafted from a length of an elastic material. Also, the preferred retaining strap 18 will have a means for adjusting its effective length, which could of course be of a wide variety of types. As FIG. 1 shows, the adjusting means could comprise a buckle or other member for adjustably retaining an overlapping loop portion of the retaining strap 18 so that the user could adjust the effective length of the retaining strap 18 by adjusting the amount that the loop portion overlaps.

The means by which the first and second ends 24 and 26 of the retaining strap 18 are coupled to the breathing tube 12 also could be of a variety of constructions. In this exemplary embodiment, as can be seen best in FIG. 5, the first end 24 of the retaining strap 18 is retained relative to the breathing tube 12 by a post 58 that has first and second ends 60 and 62 retained in corresponding bore holes in the breathing tube 12. Most preferably, there will be incorporated a means for removably and replacably retaining the first and second ends 24 and 26 of the retaining strap 18 relative to the breathing tube 12. In this embodiment, that means is carried out by having the post 58 be formed of first and second members that are resiliently compressible relative to one another. With this, the post 58 can be disengaged from the breathing tube 12 simply by compressing the first and second members. With the post 58 disengaged, the first or second end 24 or 26 of the retaining strap 18 can be slipped off to be removed, replaced, or otherwise manipulated.

Turning to FIG. 10, one sees that certain embodiments of the respirator 10 could further include a mouthpiece 70 to accommodate user preferences or, if necessary, to comply with any applicable rules or regulations. The mouthpiece 70 could, of course, be of substantially any type. For example, the mouthpiece 70 could simply comprise a loose-fitting filtering mouthpiece, similar to a dust mask. Alternatively, the mouthpiece 70 could be a tight-fitting mouthpiece in that it could form a complete seal with the wearer's face. In any event, the mouthpiece 70 in this embodiment is retained relative to the breathing tube 12 such as by tabs 72 that could be fixed, for example, to the lower ends of the first and second nasal inserts 30 and 32. To provide proper contact between the mouthpiece 70 and the wearer's face, there could be provided further one or more retaining bands 74 with first and second ends coupled to the mouthpiece 70 and a body portion for passing around a wearer's head, for being coupled to the breathing tube 12, or for otherwise providing support to the mouthpiece 70.

It will be appreciated that the respirator 10 has been described and shown primarily as a negative pressure respirator in that the air pressure inside the breathing tube 12 and the wearer's nose would be negative during inhalation with respect to the ambient air pressure outside the respirator 10. However, it must be clear that embodiments of the invention could well be crafted where the respirator 10 incorporates an atmosphere-supplying respirator, such as a positive pressure respirator in which the pressure inside the breathing tube 12 during inhalation would exceed the ambient air pressure outside the respirator 10 by any appropriate atmosphere supplying means. By way of example, the respirator 10 could comprise a pressure demand respirator in that a positive pressure atmosphere-supplying means could admit breathing air to the breathing tube 12 when the positive pressure is reduced inside the breathing tube 12 by inhalation. These and still further embodiments could certainly take advantage of the present invention for a respirator 10.

With a plurality of preferred embodiments of the invention disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein.

Accordingly, it will be clear that those with major features of the invention in mind could craft embodiments that incorporate those major features while not incorporating all of the features included in the preferred embodiments. Therefore, the following claims are intended to define the scope of protection to be afforded the inventors. Those claims shall be deemed to include equivalent constructions insofar as they do not depart from the spirit and scope of the invention.

It must be further noted that a plurality of the following claims may express certain elements as means for performing a specific function, at times without the recital of structure or material. As the law demands, these claims shall be construed to cover not only the corresponding structure and material expressly described in this specification but also equivalents thereof.

I claim as deserving the protection of Letters Patent:

1. A respirator for enabling a wearer to inhale filtered air through the wearer's nostrils, the respirator comprising:
   an elongate breathing tube with at least a proximal portion, a first distal end, and a body portion;
   at least a first air-purifying element disposed in fluidic engagement with the elongate breathing tube for purifying air that is drawn through the first air-purifying element;
   first and second nasal inserts disposed in fluidic engagement with the elongate breathing tube and with the first air-purifying element wherein the first nasal insert is disposed in close proximity to the second nasal insert and wherein each of the first and second nasal inserts includes a means for fluidically engaging a wearer's nostril;
   whereby a wearer can simultaneously engage each of the means for fluidically engaging the wearer's nostril with the wearer's nostrils and whereby the wearer can inhale purified air into the wearer's nostrils through the nasal inserts from the elongate breathing tube after the air has been purified by being drawn through at least the first air-purifying element; and
   wherein the first air-purifying element is coupled to the first distal end of the elongate breathing tube and further comprising a means for rendering the body portion of the elongate tube capable of exhibiting plastically deformable shape retention whereby the relative shape and orientation of the elongate tube and location and orientation of the first air-purifying element can be selectively adjusted.

2. The respirator of claim 1 wherein the first and second nasal inserts are disposed in the proximal portion of the elongate breathing tube, wherein the body portion of the elongate breathing tubes comprises a first branch terminating in the first distal end of the elongate breathing tube and a second branch terminating in a second distal end of the elongate breathing tube, and further comprising a second air-purifying element coupled to the second distal end of the elongate breathing tube wherein the second distal end of the elongate breathing tube is separate and distinct from the first distal end thereof.

3. The respirator of claim 1 wherein the means for rendering the body portion of the elongate tube capable of exhibiting plastically deformable shape retention comprises an elongate core member longitudinally associated with the elongate tube.

4. The respirator of claim 3 wherein the elongate core member is embedded in the elongate tube.

5. The respirator of claim 3 wherein the elongate core member is formed from metal wire.

6. The respirator of claim 1 wherein the means for rendering the body portion of the elongate tube capable of exhibiting plastically deformable shape retention comprises a material selection for at least a portion of the body portion of the elongate tube.

7. The respirator of claim 1 wherein the means for fluidically engaging a wearer's nostril of each of the first and second nasal inserts comprises a nose plug extending from each of the first and second nasal inserts, wherein the first and second nasal inserts are rotatably retained relative to the elongate tube, and wherein the nose plugs are eccentrically disposed relative to the first and second nasal inserts whereby an effective distance between the first and second nose plugs can be selectively adjusted by a rotation of one or both of the first and second nasal inserts.

8. The respirator of claim 1 wherein the first and second nasal inserts have at least a first exhaust valve in fluid association therewith whereby air can be exhaled from the wearer's nostrils and through the first exhaust valve.

9. The respirator of claim 8 wherein the first exhaust valve comprises a one-way valve to prevent unfiltered air from entering the breathing tube.

10. The respirator of claim 1 wherein the means for fluidically engaging a wearer's nostril of each of the first and second nasal inserts comprises a nose plug extending from each of the first and second nasal inserts and further comprising a means for preventing unfiltered air from passing between the nose plugs and the wearer's nostrils.

11. The respirator of claim 10 wherein the means for preventing unfiltered air from passing between the nose plugs and the wearer's nostrils comprises first and second sealing sleeves for surrounding the nose plugs.

12. The respirator of claim 11 further comprising a bridge member coupling the first and second sealing sleeves.

13. The respirator of claim 11 wherein the first and second sealing sleeves are formed from a resiliently compressible material.

14. The respirator of claim 13 wherein the first and second sealing sleeves are formed from viscoelastic foam.

15. The respirator of claim 1 wherein the first air-purifying element comprises a canister casing that retains a volume of filtering material.

16. The respirator of claim 15 wherein the first air-purifying element has a male projection extending therefrom for matingly engaging the distal end of the breathing tube.

17. The respirator of claim 16 further comprising positive engaging elements on the male projection from the first air-purifying element.

18. The respirator of claim 16 further comprising score lines spaced along the body portion of the breathing tube for enabling and guiding any necessary or desirable trimming of the breathing tube.

19. The respirator of claim 1 further comprising a retaining strap with a first end, a second end, and a body portion for securing the breathing tube to a wearer's head wherein the first and second ends of the retaining strap are coupled to the breathing tube.

20. The respirator of claim 19 wherein the first and second ends of the retaining strap are each retained by a post that is removably and replacably coupled to the breathing tube and wherein the first and second ends of the retaining strap are removably and replacably associated with the post whereby the first and second ends of the retaining strap can be removed and replaced relative to the breathing tube.

21. The respirator of claim 1 further comprising a mouthpiece coupled to the breathing tube for shielding a wearer's mouth.

22. The respirator of claim 21 wherein the mouthpiece comprises a filtering mouthpiece.

23. The respirator of claim 1 wherein the respirator comprises a negative pressure respirator.

24. A respirator for enabling a wearer to inhale filtered air through the wearer's nostrils, the respirator comprising:

an elongate breathing tube with a first distal end, a second distal end separate and distinct from the first distal end, and a body portion comprising a first branch that terminates in the first distal end of the elongate breathing tube, a second branch that terminates in the second distal end of the elongate breathing tube, and a proximal portion;

a first air-purifying element disposed adjacent to the first distal end of the elongate breathing tube and in fluidic engagement with the first branch of the elongate breathing tube for purifying air that is drawn through the first air-purifying element;

a second air-purifying element disposed adjacent to the second distal end of the elongate breathing tube and in fluidic engagement with the second branch of the elongate breathing tube for purifying air that is drawn through the second air-purifying element;

first and second nasal inserts disposed in fluidic engagement with the proximal portion of the elongate breathing tube and with the first and second air-purifying elements wherein the first nasal insert is disposed in close proximity to the second nasal insert and wherein each of the first and second nasal inserts includes a means for fluidically engaging a wearer's nostril;

whereby a wearer can simultaneously engage each of the means for fluidically engaging the wearer's nostril with the wearer's nostrils and whereby the wearer can inhale purified air into the wearer's nostrils through the nasal inserts from the elongate breathing tube after the air has been purified by being drawn through the first and second air-purifying elements.

25. The respirator of claim 24 wherein the first air-purifying element is coupled to the first distal end of the elongate breathing tube and wherein the second air-purifying element is coupled to the second distal end of the elongate breathing tube and further comprising a means for rendering the body portion of the elongate tube capable of exhibiting plastically deformable shape retention whereby the relative shape and orientation of the elongate tube and location and orientation of the first and second air-purifying elements can be selectively adjusted.

26. The respirator of claim 25 wherein the means for rendering the body portion of the elongate tube capable of exhibiting plastically deformable shape retention comprises an elongate core member longitudinally associated with the elongate tube.

27. The respirator of claim 26 wherein the elongate core member is embedded in the elongate tube.

28. The respirator of claim 27 wherein the elongate core member is formed from metal wire.

29. The respirator of claim 25 wherein the means for rendering the body portion of the elongate tube capable of exhibiting plastically deformable shape retention comprises a material selection for at least a portion of the body portion of the elongate tube.

30. The respirator of claim 24 wherein the means for fluidically engaging a wearer's nostril of each of the first and second nasal inserts comprises a nose plug extending from each of the first and second nasal inserts, wherein the first and second nasal inserts are rotatably retained relative to the elongate tube, and wherein the nose plugs are eccentrically disposed relative to the first and second nasal inserts whereby an effective distance between the first and second nose plugs can be selectively adjusted by a rotation of one or both of the first and second nasal inserts.

31. The respirator of claim 24 wherein the first and second nasal inserts have at least a first exhaust valve in fluidic association therewith whereby air can be exhaled from the wearer's nostrils and through the first exhaust valve.

32. The respirator of claim 31 wherein the first exhaust valve comprises a one-way valve to prevent unfiltered air from entering the breathing tube.

33. The respirator of claim 24 wherein the means for fluidically engaging a wearer's nostril of each of the first and second nasal inserts comprises a nose plug extending from each of the first and second nasal inserts and further comprising a means for preventing unfiltered air from passing between the nose plugs and the wearer's nostrils.

34. The respirator of claim 33 wherein the means for preventing unfiltered air from passing between the nose plugs and the wearer's nostrils comprises first and second sealing sleeves for surrounding the nose plugs.

35. The respirator of claim 34 further comprising a bridge member coupling the first and second sealing sleeves.

36. The respirator of claim 34 wherein the first and second sealing sleeves are formed from a resiliently compressible material.

37. The respirator of claim 36 wherein the first and second sealing sleeves are formed from viscoelastic foam.

38. The respirator of claim 24 wherein the first and second air-purifying elements each comprise a canister casing that retains a volume of filtering material and wherein the first and second air-purifying elements each have a male projection extending therefrom for matingly engaging the first and second distal ends of the breathing tube.

39. A respirator for enabling a wearer to inhale filtered air through the wearer's nostrils, the respirator comprising:

an elongate breathing tube with a first distal end, a second distal end separate and distinct from the first distal end, and a body portion comprising a first branch that terminates in the first distal end of the elongate breathing tube, a second branch that terminates in the second distal end of the elongate breathing tube, and a proximal portion;

a first air-purifying element fluidically coupled to the first distal end of the first branch of the elongate breathing tube for purifying air that is drawn through the first air-purifying element;

a second air-purifying element fluidically coupled to the second distal end of the second branch of the elongate breathing tube for purifying air that is drawn through the second air-purifying element;

first and second nasal inserts disposed in fluidic engagement with the proximal portion of the elongate breathing tube and with the first and second air-purifying elements wherein the first nasal insert is disposed in close proximity to the second nasal insert, wherein each of the first and second nasal inserts includes a nose plug extending from the nasal insert for fluidically engaging a wearer's nostril whereby a wearer can simultaneously engage each of the means for fluidically engaging the wearer's nostril with the wearer's nostrils and whereby the wearer can inhale purified air into the wearer's nostrils through the nasal inserts from the elongate breathing tube after the air has been purified by being drawn through the first and second air-purifying elements, wherein the first and second nasal inserts are rotatably retained relative to the elongate tube, and wherein the nose plugs are eccentrically disposed relative to the first and second nasal inserts whereby an effective distance between the first and second nose plugs can be selectively adjusted by a rotation of one or both of the first and second nasal inserts;

at least a first one-way exhaust valve in fluidic association with the first and second nasal inserts whereby air can be exhaled from the wearer's nostrils and through at least the first exhaust valve and whereby unfiltered air is prevented from entering the breathing tube; and a means for rendering the body portion of the elongate tube capable of exhibiting plastically deformable shape retention whereby the relative shape and orientation of the elongate tube and location and orientation of the first and second air-purifying elements can be selectively adjusted.

40. The respirator of claim 39 wherein the means for rendering the body portion of the elongate tube capable of exhibiting plastically deformable shape retention comprises an elongate core member longitudinally associated with the elongate tube.

41. The respirator of claim 39 wherein the means for rendering the body portion of the elongate tube capable of exhibiting plastically deformable shape retention comprises a material selection for at least a portion of the body portion of the elongate tube.

42. The respirator of claim 39 further comprising first and second sleeves of resiliently compressible material surrounding the first and second nose plugs for preventing unfiltered air from passing between the nose plugs and the wearer's nostrils.

* * * * *